United States Patent [19]

Greenwold et al.

[11] Patent Number: 4,889,134
[45] Date of Patent: Dec. 26, 1989

[54] DEVICE FOR MEASURING MULTIPLE CHANNELS OF HEARTBEAT ACTIVITY AND ENCODING INTO A FORM SUITABLE FOR SIMULTANEOUS TRANSMISSION OVER

[75] Inventors: Douglas J. Greenwold; Herbert E. Reinhold, Jr., both of Rockville, Md.

[73] Assignee: Survival Technology, Inc., Bethesda, Md.

[21] Appl. No.: 172,924

[22] Filed: Mar. 25, 1988

[51] Int. Cl.$^4$ .............................................. A61B 5/04
[52] U.S. Cl. .................................. 128/696; 128/710; 128/904
[58] Field of Search ............... 128/696, 702, 904, 710, 128/711; 364/413.05, 413.06; 346/33 ME

[56] References Cited

U.S. PATENT DOCUMENTS

| | | | |
|---|---|---|---|
| 3,132,643 | 5/1964 | Baum | 128/696 |
| 3,792,700 | 2/1974 | Sarnoff | 128/696 |
| 3,910,260 | 10/1975 | Sarnoff | 128/696 |
| 3,938,507 | 2/1976 | Sarnoff | 128/696 |
| 4,004,577 | 1/1977 | Sarnoff | 128/696 |
| 4,141,351 | 2/1979 | James et al. | 128/904 |
| 4,164,215 | 8/1979 | Finlayson | 128/696 |
| 4,173,971 | 11/1979 | Karz | 128/711 |
| 4,183,354 | 1/1980 | Sibley et al. | 128/711 |
| 4,535,783 | 8/1985 | Marangoni | 128/711 |
| 4,550,370 | 10/1985 | Baker | 128/419 P |
| 4,592,018 | 5/1986 | Wiegman | 365/63 |
| 4,593,702 | 6/1986 | Kepski | 128/696 |
| 4,622,979 | 11/1986 | Katchis | 128/702 |
| 4,633,881 | 1/1987 | Moore et al. | 128/710 |
| 4,658,830 | 4/1987 | Sarnoff | 128/696 |
| 4,679,144 | 7/1987 | Cox | 128/702 |
| 4,696,306 | 9/1987 | Shiozaki | 128/710 |
| 4,722,349 | 2/1988 | Baumberg | 128/904 |
| 4,794,532 | 12/1988 | Leckband et al. | 364/413.06 |

Primary Examiner—Francis Jaworski
Assistant Examiner—George Manuel
Attorney, Agent, or Firm—Cushman, Darby & Cushman

[57] ABSTRACT

A device for measuring electrical activity of the heart of a user. The portable device includes structure for receiving at least two leads of electrical activity of the heart of the user. This information is amplified, and coupled to a memory to produce audio signals of a form suitable for transmission over telephone lines in response to input signals. These input signals can be either from the memory or from the output of the amplifier, depending on the mode being commanded. A control structure commands the mode of operation. Live mode allows the acquired input to pass directly to the speaker, to be passed over the telephone lines. Recording mode records the input. Time interval mode records the entire capacity of the memory once. Rolling mode continually acquires and displaces other information that was previously in place. The device plays back a plurality of channels from the memory simultaneously over the telephone line so that these plurality of channels are received by the other end in a synchronized fashion. In addition, the device can operate in either a silent mode, in which information is recorded without any audio information being produced, or a sound mode in which audio information indicative of the information that is being stored is produced.

29 Claims, 2 Drawing Sheets

DEVICE FOR MEASURING MULTIPLE CHANNELS OF HEARTBEAT ACTIVITY AND ENCODING INTO A FORM SUITABLE FOR SIMULTANEOUS TRANSMISSION OVER

FIELD OF THE INVENTION

The present invention relates to a device which acquires and selectively stores multiplicity of channels of electrical heartbeat activity and encodes these channels into a form suitable for transmission over a telephone line. More specifically, the present invention relates to a portable device of this type and is adapted to be carried by the user wherever the user goes.

BACKGROUND AND SUMMARY OF THE INVENTION

The type of device herein contemplated has particular utility in two distinct medical situations. The first situation is the type referred to in commonly assigned U. S. Pat. Nos. 3,910,260, 4,004,577, and 4,658,830. Briefly stated, in this use the device is given to designated coronary prone patients together with autoinjectors containing an antiarrythmia agent (Lidocaine) and/or a thrombolytic agent (t-PA). When the patient begins to experience symptoms of a heart attack, the patient immediately goes to the phone, calls a pre-existing central source having the patient's full medical history and standing orders of the patient's doctor. The patient then connects the electrodes of the device to his skin, e.g. armpits (see U. S. Pat. No. 3,792,700) and transmits the EKG thus acquired to the central source. The experts at the central source are then immediately able to advise the patient by virtue of the EKG information conveyed and the oral descriptions of the patient provided over the phone by the patient. Under some circumstances the advice may be for the patient to self-administer the medicament by simply operating the autoinjector. The use herein contemplated is under emergency conditions where time is of the essence.

The other use of the device is as a diagnostic adjuvant. For example, where a patient is suffering heart palpitations or other unusual events, it is desirable in diagnosing the problem to have an EKG record of the event as it is taking place. While time is of the essence in capturing the event, generally speaking an emergency situation does not prevail. Devices which have been developed for this specific use have included the capability of storing acquired electrical activity of the event for immediate play back.

As indicated it is desirable to obtain as much EKG information as can be conveniently acquired to allow a qualified medical professional to diagnose exactly what problem is occurring in the user. To do this, it is desirable to obtain many views of the heart of the user. There are many standard views of the heart which will now be explained with reference to FIG. 1.

FIG. 1 shows a stick figure diagram of a user 1 and his heart 2. A first electrode RA is shown on right arm 3 of the user. A second electrode LA is shown on left arm 4 of the user. In correspondence with the standard convention, a third electrode LL is shown on the left leg 6 of the user. A plurality of views of the heart can be obtained from these three electrodes. A first view I is established between the right arm electrode RA and left arm electrode LA. A second view II is established between the right electrode RA and the left leg electrode LL. A third view III is established between the left arm electrode and the left leg electrode. This yields three standard views of the heart. In addition, other aspects of the electrocardiograph can be obtained by center tapping between two of the electrodes and using this as an reference for the other electrode. This gives three more "augmented" views. Other views are possible by using a wye configuration, and by further electrodes V1-V6 on the chest, and by other techniques which are known in the art. It is desirable for a skilled medical practitioner to have a plurality of such views of the heart during an episode, so that he may more accurately determine the occurrences during this episode.

In accordance with the present invention, it is an object thereof to provide a portable unit which can easily be carried by the user anywhere that the user goes. This portable unit desirably should provide at least two views of the heart and preferably three to provide a skilled practitioner with sufficient information about the episode.

Moreover, when a user first begins the episode, it is desirable to obtain the information immediately. The portable unit of the present invention is adapted to play this information over a telephone line, to enable medical personnel who are standing by to immediately diagnose the problem. In emergency operations, the current heart activity is played over the telephone. However, if the user must find and get to a telephone before he can play back the heart electrical activity, the episode may be over and the medical personnel would be without sufficient information upon which to make a diagnosis. Therefore, according the present invention, information is stored in the memory means upon an initiation by the user. Therefore, when the user feels an episode beginning, the user can initiate the memory means to begin storing. Upon reaching a telephone, the user can play back the information from the memory device to the practitioners.

This has posed another problem in the prior art. Assuming that a device were known to play back multiple views of the heart, the prior art would play back these multiple views one after the other. This provides the practitioner with the desired information, but makes it very difficult for the practitioner to synchronize this information. Moreover, this lengthens the time necessary to make the diagnosis by the number of channels that will be received. In fact, if the two channels are sequentially received, the practitioner receiving both items of information would have to manually synchronize them, holding them together with tape or the like. This makes for difficult synchronization. Accordingly, the present invention includes a feature such that the multiple channels of information which are stored in the memory are simultaneously transmitted over the telephone lines. This produces a presynchronized print-out at the practitioner's end, simplifying the diagnosis for the practitioner.

The present invention also operates in a "rolling mode" where the memory is continuously storing information indicative of the electrical activity of the heart. This enables crucial information to be unambiguously stored. By the time a user feels an episode onset, the episode has already begun. The user would miss the beginning portion of this episode if he were merely to initiate the recording sequence when he felt the onset of the episode. To solve this problem, the present invention uses a rolling mode of recording. This recording mode continuously records electrical activity of the heart. New electrical activity is recorded to displace old electrical activity, therefore continuously rolling through the memory from beginning to end. Upon feeling the onset of an episode, the user can initiate the rolling recording initiation. This causes the memory to retain a certain amount of information before the initiation (e.g. 30 seconds) and to record a certain amount of information after the initiation. When the user then plays this information back over the telephone, the information includes some time before the initiation and the crucial part of the information.

Such a rolling mode has, however, been known in the art. For instance, U.S. Pat. No. 4,622,979 describes a user worn apparatus which records in a mode very similar to rolling mode. However, a problem exists in the use of this device. Specifically, the rolling mode continuously records information, and therefore the memory is always full with this information. When a user goes to play back the information, however, it is crucial that the information which is played back is the information which has most recently been recorded. Since the memory is always full, the user may be playing back information indicative of a previous episode. The present invention obviates this disadvantage by including a erase-after-record mode. This mode allows the information to be played back and then elapses a certain amount of time. An elapse of this certain amount of time is necessary to ensure that the receiving end has received the information properly, and that another playback will not be necessary. After this time is elapsed, this mode automatically erases the contents of the memory. Therefore, it becomes impossible for user to later play this back while erroneously thinking it is the current information.

Heart patients also typically do not want to cause a commotion by having others around them thinking that they are beginning to undergo a heart attack. However, previous portable information devices have made an audio sound while they record the heart attack information. If a user thinks he is going to cause a commotion by recording the onset of an episode, this user will have a more difficult choice to make. Should he begin recording the episode and cause himself possible embarrassment, or is this really an episode at all? Users should never be faced with such choice, as they should always be recording every episode which could possibly occur. Therefore, the present invention also includes another advantageous mode wherein a single episode can be recorded with speaker-off. In this way, the user will be spared any possible embarrassment. This leads the user to more likely record the information.

Devices which are superficially similar to the present invention are also known to the inventors of the present invention. One such item is the retrospective (TM) ECG memory loop recorder marketed by Cardiac Evaluation Center Incorporated, Milwaukee, Wis. 53222. This device reads a plurality of channels of information and also operates in a similar rolling mode. This device also recognizes the problem of sending old data erroneously, when intending to send current data but merely relies on some manual tone played to the user to ensure against it. There is absolutely no way to automatically cause the retrospective device to automatically erase. This device uses a dual channel mode and recognizes that this enhances diagnosis. However, in order to maintain this device compatible with single channel receivers, it transmits 30 seconds of channel 1 and then 30 seconds of channel 2. This has disadvantages discussed above, in that the practitioner must somehow evaluate this information. The Memorytrace (TM) unit by Cardiocare also has dual channel recording capability. This device also operates in a equivalent to the rolling mode. However, this device also does not include the advantageous features discussed above.

U.S. Pat. No. 4,550,370 also relates to a similar system.

U.S. Pat. No. 4,679,144 relates to a system which obtains information for real time analysis of EKG information. This information is A to D converted and stored in a RAM for later read out. However, the advantages of the present invention are not obtained.

Similar devices are also described in U.S. Pat. Nos. 4,535,783; 4,592,018; 4,164,215; 4,593,702; and 3,132,643. However, none of these patents teach advantageous features of the present invention. A particularly preferred embodiment of this invention uses underarm or armpit electrodes such as the type described in U.S. Pat. No. 3,938,507, the disclosure of which is hereby incorporated by reference. In combination with these two armpit electrodes, the most preferred embodiment of the present invention uses a third electrode to operate as the LL electrode. This third electrode is adapted to be inserted into the belt of a user to provide multiple views of the heart.

A two electrode system is also described in our copending application "MONITORING DEVICE WITH DUAL POSITION ELECTRODES", inventors H.E. Reinhold and D.J. Greenwold, filed Mar. 25, 1988, Ser. No. 07/172,840, the disclosure of which is expressly incorporated herein by reference.

Specifically, the present invention relates to a portable measuring device for measuring the electronic activity of the heart of the user. This device includes a connector for receiving signals indicative of at least two electrical leads o activity of the heart of the user. These signals are amplified to produce at least first and second electrical activity signals. These electrical activity signals, as amplified, are then stored in a memory. An audio information producing structure is provided that produces audio signals of a form suitable for transmission over the telephone lines. A control device controls the operation of this whole apparatus. A first mode of the control device allows the device to operate in a live mode by connecting signals from the input of the memory to the audio information producing device. Thereafter, the signals which are obtained on the connector are connected directly to the audio information producing device. A second mode commands the memory to record in the rolling mode in which information is continuously being stored in the memory, new information erasing previous information. A third mode commands the memory to store information for a time interval. This third mode can be operated with the audio information producing structure either on (producing audio information) or off (silent). A playback mode includes at least a simultaneous mode in which information from the two channels is simultaneously played back over the telephone line.

According to another aspect of the invention, this operation can also follow a sequential mode where the first channel played back is followed by a second channel being played back.

Yet another aspect of the invention erases the contents of the memory some predetermined time after sending. The memory means is preferably a digital memory, so that an A to D converter and D to A converter may be used to interface with this memory means. The amplifying means is preferably a differential amplifier while the audio information producing means includes a voltage controlled oscillator operating at 1700 hertz and an audio amplifier and speaker.

BRIEF DESCRIPTION OF THE DRAWINGS

An exemplary and presently preferred embodiment of this invention will be described in detail with reference to the accompanying drawings, wherein.

DETAILED DESCRIPTION OF THE PREFERRED EMBODIMENT

A presently preferred embodiment of the invention will now be described.

Figure 2:
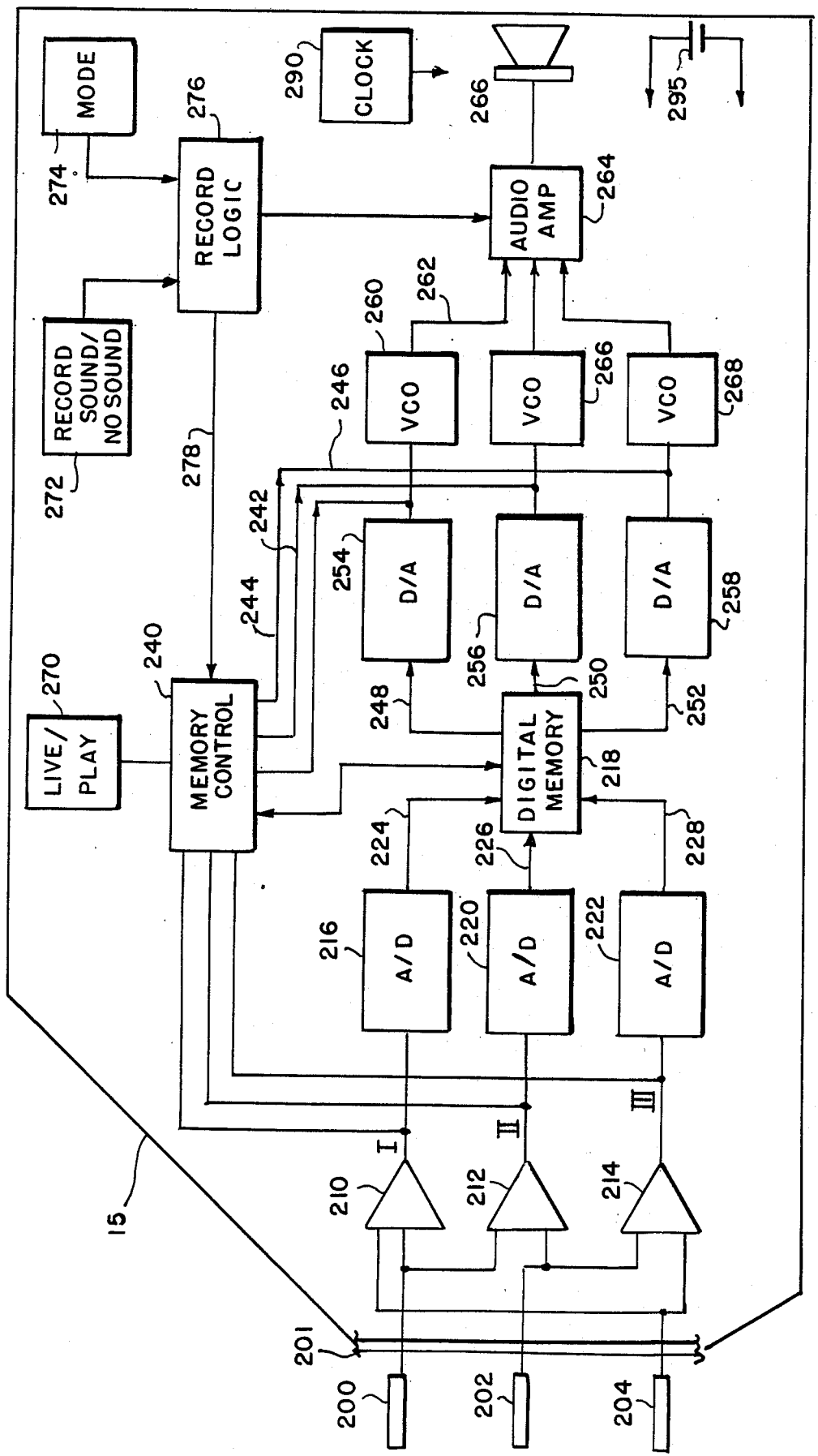
FIG. 2 shows a block diagram of the system.

FIG. 2 shows a block diagram of the preferred embodiment of the present invention. The invention requires signals from at least two electrodes 200 and 202, but electrode 204 is also shown in this preferred embodiment entering connector 201. A three electrode system acquires three channels, while a standard four electrode system can acquire two channels, the connector 201 is shown as a detachable plug in our co-pending application "MONITORING DEVICE WITH DUAL POSITION ELECTRODES", inventors H.E. Reinhold and D.J. Greenwold, filed Mar. 25, 1988, Ser. No. 07/172,840. This plug carries only two electrodes. The present invention can carry four standard electrodes or a three electrode system of the armpit type. Signals from the various electrodes are connected to a plurality of differential amplifiers 210, 212 and 214. The output of each of the amplifiers represents one lead of electrical activity of the heart.

The output of differential amplifier 210 is connected to A to D converter 216 which converts the output of differential amplifier 210 to a digital signal. This digital signal is coupled to digital memory 218 which stores the digital signal. In a similar fashion, the output of amplifier 212 is A to D converted by converter 220 and the output of amplifier 214 is A to D converted by converter 222. The digital outputs of all of these converters are coupled to the same digital memory with 218, which therefore stores all of the signals representing the outputs of the three channels I-III.

The operation of the digital memory is controlled by memory control device 240. This device interfaces with digital memory 218 to command digital memory 218 to store the respective outputs 224, 226 and 228 from A to D converters 216, 220, and 222 respectively.

Memory control 240 also includes a plurality of inputs from lines I, II and III respectively. These lines are the same lines that are also input to A to D converters 216, 220 and 222 respectively. Memory control 240 has an internal switch which can be activated to switch line I (input to A to D converter 216) through to line 242. Line II is also switched to line 244 and line III is switched to line 246. This has the effect of bypassing the A to D conversion, digital memory 218, and D to A conversion. This will be described in more detail herein.

The outputs of digital memory 218 appear on lines 248, 250 and 252. Line 248 is a digital output including the information in digital memory 218 indicative of channel I. This information is coupled to D to A converter 254. Lines 250 and 252 are connected to corresponding D to A converters 256 and 258 respectively. The output of D/A 254 is an analog signal, and is connected to a voltage controlled oscillator (VCO) 260. Voltage controlled oscillator 260 produces an output signal which has a center frequency at a predetermined frequency, and which is modulated by the output of D to A converter 254. VCO 260 produces a output on line 262 which is coupled to an audio amplifier 264. The output of audio amplifier 264 is an electrically encoded audio signal. This is used to drive speaker 266 to produce an audio output. The audio output signal produced by speaker 266 must be an audio signal of a form suitable for transmission over telephone lines.

D to A converter 256 has a corresponding VCO 266 and D to A converter 258 has a corresponding VCO 268.

The output signals of VCOs 260, 266 and 268 may be merely combined into audio amplifier 264, or may be selectively received by audio amplifier 264. In the latter case, audio amplifier 264 includes a multiplexer-type structure to selectively switch between input signals. If the signals are to be merely combined, VCOs 260, 266 and 268 must operate at different center frequencies. In this embodiment, the center frequencies at which these structures operate are 1100 hertz, 1700 hertz and 2400 hertz, respectively. An analog addition can then be performed between the different signals.

In a parallel mode operation, the outputs from all three channels I-III are simultaneously read from the digital memory, and are encoded through audio amplifier 264 onto speaker 266 which produces a parallel output of all channels over the telephone line. A sequential mode of operation reads all of channel I from digital memory 218 first. All of channel I is then sent to D to A 254, through VCO 260 into audio amp 264 and encoded onto the telephone line. After all of channel I is read, and only then, is channel II readout begun. This facilitates reception at the practitioner end, but increases the reception time and makes the synchronization of these signals more difficult. It is desirable for the practitioner to see all of the channels received simultaneously, and to see the relationships between the various channels. This can be done in the sequential mode by receiving all of one channel, then receiving all of another channel, then receiving all of a third channel, and then cutting and pasting the three channels together. It is very difficult to accurately align these three channels, but it can be done. The operation is greatly facilitated if the three channels are simultaneously sent, so that they can be simultaneously received without any such cutting and pasting being necessary.

A particularly preferred embodiment of this invention uses underarm or armpit electrodes made out of carbon particles impregnated in vinyl, such as the type described in U.S. Pat. No. 3,938,507. In combination with these two armpit electrodes which are configured to be comfortably worn under the arm of a user, the most preferred embodiment of the present invention uses a third electrode to operate as the LL electrode. This third electrode is adapted to be inserted into the belt of a user to provide multiple views of the heart. The waist electrode can be constructed as the underarm electrode described in U.S. Pat. No. 3,938,507. This electrode can be held in the belt area, if a belt is not present.

Memory control 240 performs a plurality of functions. Digital memory is controlled by memory control signal 280. Memory control 240 provides a read/write signal to digital memory 218 as part of signal 280. A write signal command digital memory 218 to record and conversely a read signal commands digital memory 218 to play. In play mode, therefore, a read signal is sent to digital memory 218 and in record mode, a write signal is sent to memory 218. Live mode in contrast, does not require the use of memory 218 at all. Therefore, live mode causes the signals I-III to be connected around the bank including all A to D converters, digital memory 218, and all D to A converters. This causes the signals from amplifiers 210-214 to go directly to VCOs 260, 266 and 268 and to be later encoded into audio signals to be output by speaker 266.

Figure 1:
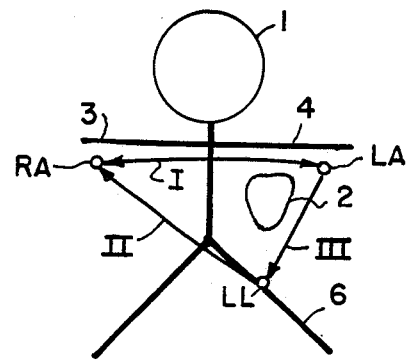
FIG. 1 shows a diagram with which leads of an electrical activity of the heart are explained.
Figure 3:
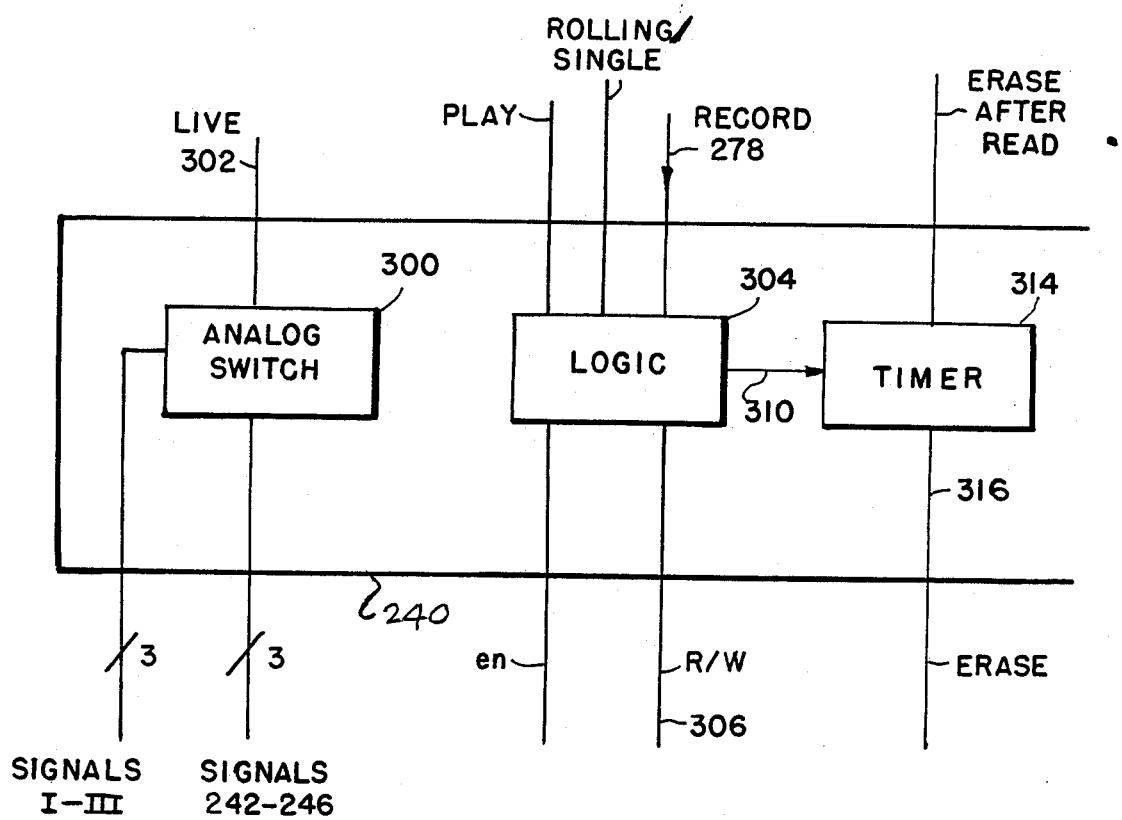
FIG. 3 shows more detail about the memory control device.

A more detailed view of memory control 240 is shown in FIG. 3. Memory control 240 receives signals I-III at one input thereof and produces signals 242-246 as an output thereof. The switching of these signals is controlled by an analog switch 300. The switch control to the analog switch is controlled from live line 302. Live line 302 can be typically controlled by a user actuated switch. When the user commands the device into live mode, analog switch 300 is switched to form a short circuit between the inputs thereof. This causes the outputs of speaker 266 to assume the states of the signals I-III. Memory control 240 also receives the play command, and the record command as inputs thereof. These two commands are combined by a logic module 304 into a single read/write signal 306. Read/write signal 306 is included as part of memory control signal 280.

The live and play inputs to memory control 240 are produced by module 270. This will typically be a module including a plurality of switches, one for live and one for play. Similarly, modules 272 and 274 includes switches to command record with sound or no sound, and to command a mode of recording, respectively. The mode switching may alternatively be performed by a switch which is included as part of connector 201. Specifically, the mode may be commanded by merely plugging in electrodes.

The record sound/no sound module 272 and mode module 274 are connected to record logic module 276. Record logic module determines from mode module 274 if the recording mode has been requested. If requested, record logic module 276 produces a record output signal 278 which is coupled to memory control 240. This signal commands memory control 240 to command digital memory 218 to record. Record logic 276 also produces an enable output to audio amplifier 264. When this signal is not present, audio amplifier 264 does not produce output sound. Therefore, when module 272 indicates sound, an output signal is produced from record logic module 276.

Mode command 274 commands whether memory 218 should be in rolling mode or in time interval mode. The rolling mode is a mode where information in the memory is continually being updated. In this embodiment, the memory can maintain approximately 70 seconds of storage time. Rolling mode begins storing information until the memory is full. At that time, the rolling mode returns to the beginning address of the memory and begins storing over the initial data that was previously stored. The effect of the rolling mode is that at any given time, the 70 seconds before the memory location which is currently being stored includes the most recent 70 seconds of heart activity.

If the device is in rolling mode, a user initiates a command at the onset of an episode. Upon initiating the command, information for some time before the initiation is retained, along with the remaining information which will fit in the memory after the initiation. As such, rolling mode enables catching the information before the command is made.

Record mode signal 278 also includes information on whether rolling mode should be initiated. Logic module 304 determines whether rolling mode should be initiated from signal 278. Logic module 304 also produces an enable signal. This enable signal defines whether rolling mode is commanded. Digital memory 218 continually stores new information in rolling mode, while it stores only information indicative of one period of the memory in time interval record mode.

Mode module 274 can also include a switch to command automatic erase-after-write function. In this case, memory control 240 must include additional structure. Logic module 304 produces a signal 310 after the completion of a play cycle. This signal 310 indicates that the play cycle has been completed. This is input to timer 314 which begins counting a predetermined time interval. In this embodiment, the predetermined time interval is 60 seconds. Signal 310 remains active once a play cycle is complete as long as another play command is not received into logic module 304. Timer 314 counts as long as signal 310 remains active. If signal 310 remains active for the full time count of timer 314, an output signal 316 is produced thereby. This output signal is an erase signal, and is included as part of signal 280. The erase signal commands digital memory 218 to erase its entire contents.

The entire system of FIG. 2 is synchronized by a clock 290. Those having ordinary skill in the art would understand the specific structures which need to be synchronized by the clock, and therefore the specific connections have not been detailed herewith. The preferred embodiment of the present invention performs all the switching functions in memory control 240 and record logic 276 using a gate erase structure.

The entire device is housed in a housing 15, and powered by a battery 295.

Of course, many modifications are possible in this embodiment, and such modifications are intended to be encompassed within this invention. Although only a few exemplary embodiments of this invention have been described in detail, those skilled in the art will readily appreciate that such many modifications could be easily encompassed in these exemplary embodiments without materially departing from the novel teachings and advantages of this invention. For instance, an analog memory 218 could easily be used without the use of A to D converters and D to A converters. Amplifiers other than a differential amplifier could be used. In addition, the system could be used with two channels, or with any other number of channels more than three channels. A ground reference could also be used so that differential amplifiers having a lower common mode rejection are possible.

Accordingly, all such modifications are intended to be encompassed within the invention as defined in the following claims.

What is claimed is:

1. A portable measuring device for acquiring, storing and transmitting electrical activity of a heart of a user comprising: connector means for receiving signals indicative of at least two leads of electrical activity of the heart of the user;

means for amplifying said signals to produce at least first and second electrical activity signals from said signals indicative of at least two leads of electrical activity;

memory means, coupled to said amplifying means to receive said first and second electrical activity signals at an input thereof, for storing information indicative of said first and second electrical activity signals;

audio information producing means for selectively producing audio signals of a form suitable for transmission over telephone lines in response to input signals to be transmitted; and control means for controlling operation of said device, coupled to said memory means and said audio information producing means, comprising:

(a) first means for commanding said device to operate in a live mode by connecting said at least first and second electrical activity signals which are currently being produced by said amplifying means to said audio information producing means as said input signals thereto, so that said audio information producing means produces audio signals indicative of said at least first and second electrical activity signals simultaneously for transmission over said telephone lines;

(b) second means for commanding said memory means to record said first and second electrical activity signals; and (c) playback command means operating at least in a simultaneous mode for commanding said memory means to play back the stored information thereof in the form of input signals to said audio information producing means such that said audio information producing means produces audio signals indicative of said at least first and second electrical activity signals simultaneously for transmission over said telephone lines.

2. A device as in claim 1 further comprising more than two electrodes, coupled to said connector means, for attaching to said user to measure said electrical activity of said heart thereof.

3. A device as in claim 2 wherein said second means includes means for commanding said memory means into a rolling mode where information is continually being stored in said memory means, new information erasing previous information stored during a previous time interval;

(c) third means for commanding said memory means into a time interval mode to store said at least first and second electrical activity signals for a time interval;

wherein the command of said memory means into said rolling mode by said second means and into said time interval mode by said third means is selectably connected means to respective ones of said electrodes.

4. A device as in claim 3 further comprising a switch within said connector means which is selectively actuated by a connection of said electrodes to said connector means.

5. A device as in claim 3 wherein said control means further comprises means for indicating an abnormal heart activity beginning in a rolling mode, to store a predetermined time before said beginning and a predetermined time after said beginning.

6. A device as in claim 5 wherein said predetermined time after said beginning is selectable by said selectably connected means.

7. A device as in claim 3 further comprising (d) fourth means for commanding said audio information producing means to be on or off during said time interval mode.

8. A device as in claim 2 wherein there are three electrodes, including two underarm electrodes, and a belt electrode.

9. A device as in claim 2 wherein said amplifying means comprise a plurality of differential amplifiers, coupled to said connector means, each receiving signals from at least two of said electrodes.

10. A device as in claim 1 when said memory means comprises a digital memory, an analog to digital converter connected to an output of said amplifying means for converting said output of said amplifying means to a digital signal and for providing said signal to said digital memory; and a digital to analog converter, connected to an output of said digital memory, for converting said output of said digital memory to an analog signal.

11. A device as in claim 10 wherein said first means includes means for bypassing said analog to digital converter, said memory means and said digital to analog converter.

12. A device as in claim 10 wherein said first means is coupled to said output of said amplifying means and to said audio information producing means and is operable in response to a command signal to command said device to operate in said live mode.

13. A device as in claim 1 wherein said audio information producing means comprises at least one voltage controlled oscillator, receiving the input signals to which said audio information producing means is responsive.

14. A device as in claim 13 wherein said audio information producing means further comprises an audio amplifier and a speaker.

15. A device as in claim 14 wherein each of said at least one voltage controlled oscillator operate at different frequencies, respectively.

16. A device as in claim 1 wherein said play back command means also includes means for operating said memory means in a sequential mode wherein stored information indicative of said at least first electrical activity signal is first played back, followed by stored information indicative of said at least second electrical activity signal being played back.

17. A device as in claim 16 further comprising timer means, for initiating a timer count upon play back of said memory means stored information indicative of said at least first electrical activity signal or said second electrical activity signal, and erase-after-play means, coupled to said timer means, for commanding said memory means to erase the stored information thereof after said timer count has been completed.

18. A device as in claim 17 wherein said timer means is reset by initiation of another play back command.

19. A device as in claim 18 further comprising a battery for powering said portable apparatus.

20. A device as in claim 19 further comprising a portable housing containing said connector means, said amplifying means, said memory means, said audio information means and said control means.

21. A device as in claim 1 further comprising timer means, for initiating a timer count upon play back of said memory means, and erase-after-play means, coupled to said timer means, for commanding said memory means to erase the stored information thereof after said timer count has been completed.

22. A device as in claim 21 wherein said timer means is reset by initiation of another play back command.

23. A device as in claim 1 wherein said first means is coupled to the output of said amplifying means and to said audio information producing means and is operable in response to a command signal to command said device to operate in said live mode.

24. A portable device for acquiring, storing and transmitting electrical activity of a heart of a user comprising:
   connector means for receiving signals indicative of at least two leads of electrical activity of the heart of the user;
   means for amplifying said signals to produce at least first and second electrical activity signals from said signals indicative of at least two leads of electrical activity;
   memory means, coupled to said amplifying means to receive said first and second electrical activity signals at an input thereof, for storing information indicative of said first and second electrical activity signals;
   audio information producing means for selectively producing audio signals of a form suitable for transmission over telephone lines in response to input signals to be transmitted; and
   control means for controlling operation of said device coupled to said memory means and said audio information producing means, comprising:
   (a) first means for commanding said device to operate in a live mode by connecting said at least first and second electrical activity signals which are currently being produced by said amplifying means to said audio information producing means as said input signals thereto so that said audio information producing means produces audio signals indicative of said at least first and second electrical activity signals simultaneously for transmission over said telephone lines;
   (b) second means for commanding said memory means to record information indicative of said at least first and second electrical activity signals;
   (c) play back command means for selectively commanding said memory means to play back to stored information thereof in the form of input signals to said audio information producing means, so that said audio information producing means produces audio signals indicative of said played back stored information;
   (d) timer means for initiating a timing sequence upon completion of said play back, and continuing said timing as long as another command from said play back command means is not initiated; and
   (e) erase-after-play means, coupled to said timer means, for producing a signal commanding erasure of said memory means after said timer reaches a predetermined value.

25. A device as in claim 24 wherein said first means is coupled to the output of said amplifying means and to said audio information producing means and is operable in response to a command signal to command said device to operate in said live mode.

26. A device as in claim 24 wherein said second means commands said memory means into a rolling mode where information is continually being stored in said memory means, new information erasing previous information stored during a previous time interval, and further comprising:
   (c) third means for commanding said memory means into a time interval mode to store information indicative of said at least first and second electrical activity signals for a time interval.

27. A device as in claim 24 further comprising
   (d) fourth means for commanding said audio information producing means to be on or off during commanding by said third means.

28. A portable measuring device for measuring electrical activity of a heart of a user comprising:
   connector means for receiving signals indicative of at least two leads of electrical activity of the heart of the user;
   means for amplifying said signals to produce at least first and second electrical activity signals from said signals indicative of at least two leads of electrical activity;
   memory means, coupled to said amplifying means to receive said at least first and second electrical activity signals at an input thereof, for storing information indicative of said at least first and second electrical activity signals;
   audio information producing means for selectively producing audio signals of a form suitable for transmission over telephone lines in response to input signals to be transmitted; and
   control means for controlling operation of said device, coupled to said memory means and said audio information producing means, comprising:
   (a) first means for commanding said device to operate in a live mode by connecting said at least first and second electrical activity signals which are currently being produced by said amplifying means to said audio information producing means as said input signals thereto, so that said audio information producing means produces audio signals indicative of said at least first and second electrical activity signals simultaneously for transmission over said telephone lines;
   (b) second means for commanding said memory means into a recording mode to record information indicative of said at least first and second electrical activity signals;
   (c) third means for commanding said audio information producing means to be on or off during said recording mode; and
   (d) playback command means operating at least in a simultaneous mode for commanding said memory means to play back the stored information thereof in the form of input signals to said audio information producing means such that said audio information producing means produces audio signals indicative of said at least first and second electrical activity signals simultaneously for transmission over said telephone lines.

29. A device suitable for use under emergency conditions for acquiring the electrical activity of the heart of a user in a form suitable for transmission over a telephone line comprising
   a portable housing,
   a pair of electrodes, configured to be placed within the armpits of a user and to be comfortably retained within the armpits by the user so as to acquire the electrical activity of the heart of the user, a third electrode configured to be placed on the user s skin in the waist area so as to acquire (1) in conjunction with one of said pair of electrodes a second lead of the electrical activity of the heart of the user and (2) in conjunction with the other of said pair of electrodes a third lead of the electrical activity of the heart of the user, three elongated electrical wires connected with said electrodes and with said portable housing for simultaneously transmitting the three leads of electrical activity of the heart of the user acquired by said electrodes to said portable housing, sonic speaker means carried by said housing for creating signals indicative of the simultaneous three leads of electrical activity acquired by the electrodes in a form suitable for transmission over a telephonic line, electric circuit means within said housing for transmitting the simultaneous three leads of electrical activity acquired by said electrodes and transmitted by said three electrical wires to said sonic speaker means so as to create therein signals indicative of the simultaneous three leads of electrical activity acquired by said electrodes for transmission over a telephonic line.

* * * * *